US008545786B2

(12) United States Patent
Ayers et al.

(10) Patent No.: US 8,545,786 B2
(45) Date of Patent: Oct. 1, 2013

(54) MANUFACTURE OF POROUS NET-SHAPED MATERIALS COMPRISING ALPHA OR BETA TRICALCIUM PHOSPHATE OR MIXTURES THEREOF

(75) Inventors: Reed A. Ayers, Golden, CO (US); Steven J. Simske, Fort Collins, CO (US); John J. Moore, Evergreen, CO (US); Martin Castillo, Denver, CO (US); Guglielmo Gottoli, Golden, CO (US)

(73) Assignee: Colorado School of Mines, Golden, CO (US)

( * ) Notice: Subject to any disclaimer, the term of this patent is extended or adjusted under 35 U.S.C. 154(b) by 2790 days.

(21) Appl. No.: 10/621,752

(22) Filed: Jul. 16, 2003

(65) Prior Publication Data

US 2004/0019385 A1    Jan. 29, 2004

Related U.S. Application Data

(63) Continuation-in-part of application No. 10/199,139, filed on Jul. 19, 2002, now abandoned, which is a continuation of application No. 09/957,829, filed on Sep. 21, 2001, now abandoned.

(60) Provisional application No. 60/234,841, filed on Sep. 22, 2000.

(51) Int. Cl.
*A61F 2/24* (2006.01)

(52) U.S. Cl.
USPC ............ 423/306; 264/321; 264/327; 623/11; 623/16; 623/66

(58) Field of Classification Search
USPC .......................................... 423/306; 623/23.5
See application file for complete search history.

(56) References Cited

U.S. PATENT DOCUMENTS

| 4,673,355 A | * | 6/1987 | Farris et al. ................... 433/218 |
| 5,188,678 A | | 2/1993 | Sekhar et al. |
| 5,607,474 A | | 3/1997 | Athanasiou et al. |
| 5,769,884 A | | 6/1998 | Solovay |

(Continued)

FOREIGN PATENT DOCUMENTS

WO    WO 99/34845    7/1999

OTHER PUBLICATIONS

Wong et al., "Functionally graded tricalcium phosphate/fluoroapatite composites," 2002, Materials Science and Engineering, C 20, pp. 111-115.*

(Continued)

*Primary Examiner* — Melvin C Mayes
*Assistant Examiner* — Colette Nguyen
(74) *Attorney, Agent, or Firm* — Sheridan Ross P.C.

(57) ABSTRACT

Methods for producing porous tricalcium phosphate net-shaped material are provide. The methods involve preparing a reactant mixture comprising calcium oxide and phosphorus pentoxide in a mole percent ratio that allows the mixture to form tricalcium phosphate upon combustion thereof, forming this mixture into a desired final shape in a die with compression, and carrying out a combustion synthesis therewith. Net-shaped TCP materials of the combustion synthesis, comprising alpha tricalcium phosphate or mixtures of alpha and beta tricalcium phosphate, are optionally further treated to effect transition of the alpha phase to the beta phase. The net-shaped TCP materials can have a uniform or non-uniform porosity.

27 Claims, 5 Drawing Sheets

(56) References Cited

U.S. PATENT DOCUMENTS

| | | | |
|---|---|---|---|
| 5,986,169 | A | 11/1999 | Gjunter |
| 6,019,936 | A | 2/2000 | Chung et al. |
| 6,090,732 | A * | 7/2000 | Ito et al. .......................... 501/1 |
| 6,283,997 | B1 | 9/2001 | Garg et al. |
| 6,316,091 | B1 | 11/2001 | Richart et al. |
| 6,365,149 | B2 | 4/2002 | Vyakarnam et al. |
| 6,375,877 | B2 | 4/2002 | Lauf et al. |
| 6,458,162 | B1 | 10/2002 | Koblish et al. |
| 2001/0016353 | A1 * | 8/2001 | Janas et al. .................... 435/395 |
| 2002/0125592 | A1 * | 9/2002 | Schulman et al. .............. 264/16 |
| 2002/0140137 | A1 * | 10/2002 | Sapieszko et al. ............ 264/629 |
| 2003/0069638 | A1 * | 4/2003 | Barlow et al. .............. 623/16.11 |
| 2003/0138473 | A1 * | 7/2003 | Koblish et al. ................ 424/423 |

OTHER PUBLICATIONS

Koster et al., "Experimenteller Knochenersatz durch resorbierbare Calciumphosphat-Keramik," 1976, Langenbecks Arch. Chir., 341, pp. 77-86.*

Koster et al., "Experimenteller Knochenersatz durch resorbierbare Calciumphosphat-Keramik" Translation: "Experimental Bone Replacement With Resorbable Calcium Phosphate Ceramic," 1976, Langenbecks Archiv Fuer Chirurgie, 341, pp. 77-86.*

Taboas et al., "Indirect solid free form fabrication of local and global porous, biomimetic and composite 3D polymer-ceramic scaffolds," 2003, Biomaterials, 24, pp. 181-194.*

Denissen et al., "Net-shaped hydroxyapatite implants for release of agents modulating periodontal-like tissues," 1997, J Periodont Res, 32, pp. 40-46.*

Kim et al., "Catalytically Assisted Self-Propagating High-Temperature Synthesis of Tantalum Carbide Powders," 2001, J. Am. Ceram. Soc., 84[5], pp. 976-982.*

Jie-Cai et al., "In-situ combustion synthesis and densification of TiC—xNi cermets," 2000, Materials Science and Engineering, A280, pp. 328-333.*

Koster et al., "Resorbierbare Calciumphosphatkeramik im Tierexperiment unter Belastung," 1977, Langenbecks Arch. Chir., 343, pp. 173-181.*

Koster et al., "Resorbierbare Calciumphosphatkeramik im Tierexperiment unter Belastung" Translation: "Resorbable Calcium Phosphate Ceramic in an Animal Experiment Under Load," 1977, Langenbecks Arch. Chir., 343, pp. 173-181.*

A. C. Tas, *J. Am. Ceram. Soc.*, 81(11): 2853-2863 (1998).

X. Zhang, et al., Combustion Synthesis of Advanced Porous Materials in Microgravity Environment, May 1999 (available at www.ncmt.org/events/combustion1999).

V. Brailovski and R. Trochu; *Bio-Medical of Materials and Engineering*, 6(4): 291-298 (1996).

A. C. Tas, et al., *J. Materials Science*, 8:91-96 (1997).

N. Kivrak and A.C. Tas, *J. Am. Ceram. Soc.*, 81(9): 2245-2252 (1998).

R. Cavagan, et al., *Journal of Long-Term Effects of Medical Implants*, 9(4):403-412 (1999).

A. C. Tas, *Journal of the European Ceramic Society*, 20:2389-2394 (2000).

* cited by examiner

MANUFACTURE OF POROUS NET-SHAPED MATERIALS COMPRISING ALPHA OR BETA TRICALCIUM PHOSPHATE OR MIXTURES THEREOF

CROSS-REFERENCE TO RELATED APPLICATIONS

This application is a Continuation-in-Part of U.S. patent application Ser. No. 10/199,139, filed Jul. 19, 2002 now abandoned, entitled "Non-Uniform Porosity Tissue Implant," which is a continuation of U.S. patent application Ser. No. 09/957,829, filed Sep. 21, 2001 now abandoned, entitled "Non-Uniform Porosity Tissue Implant," which claims priority to Provisional Application Ser. No. 60/234,841, filed Sep. 22, 2000, and entitled "Non-Uniform Porosity Tissue Implant," each of which is specifically incorporated herein by reference.

BACKGROUND OF THE INVENTION

1. Field of the Invention

The present invention relates to methods for producing porous tricalcium phosphate net-shaped materials comprising alpha or beta tricalcium phosphate or mixtures thereof by a combustion synthesis method.

2. Description of the Prior Art

The need for biomaterials in orthopedic and dental applications has increased as the world population ages. A significant amount of research into biomaterials for orthopedic and dental uses has attempted to address the functional criteria for orthopedic and dental reconstruction within the human body. The materials which have become available for such uses have improved in recent years. All such materials must be biocompatible, however, and the degree of biocompatibility exhibited by materials which are candidates for such use is always a major concern. Biomaterials useful for orthopedic and dental reconstructions must have high strength, must be able to be immediately affixed to the situs for reconstruction, must bond strongly to bone, and must give rise to strong, highly resilient restorations.

Tricalcium phosphate (TCP) materials are considered as one of the most preferred material types in the filed of orthopedic, restorative and reconstructive surgery, and are particularly useful for bone replacement, spinal repair, reconstructive, cosmetic and other surgeries. Tricalcium phosphate occurs in at least two forms. The first is the monoclinic form, called alpha tricalcium phosphate. The second form is the orthorhombic form, called beta tricalcium phosphate. Beta tricalcium phosphate (beta TCP) is the preferred form for bone replacements because it is capable of being resorbed by the body, facilitating bone remodeling. At appropriate porosities, beta TCP resembles natural bone and provides a scaffold for in-migration of osteogenic cells, resulting in production of bone directly attached to the beta TCP implant. The body will generally resorb beta-TCP within about two years, replacing it with natural bone.

Calcium phosphate ceramics have been fabricated and implanted in mammals in many different forms including as shaped bodies, in cements and otherwise. Different stoichiometric compositions such as hydroxyapatite (HA), tricalcium phosphate (TCP), and tetracalcium phosphate (TTCP), have all been employed to this end in an attempt to match the adaptability, biocompatibility structure and strength of natural bone. However, these ceramic biomaterials exhibited problems derived from chemical and processing shortcomings that limited stoichiometric control, crystal morphology, surface properties, and, ultimately, reactivity in the body. Intensive milling and comminution of natural minerals of varying composition was required, followed by powder blending and ceramic processing at high temperatures to synthesize new phases for use in vivo. Thus, despite tremendous efforts directed to the preparation of improved calcium phosphate and precursor hydroxyapatite materials for such uses, significant shortcomings still remain.

Current processes for preparing beta TCP implants have not yet been perfected. Two approaches have been taken toward the goal of producing TCP ceramics for use as bone replacements. The first approach has been by synthesis from aqueous solutions for use in bioceramic applications. The second approach involves sintering or sol-gel routes. The sintering process includes molding a powder to a required shape by a compacting process, then heating to a high temperature so that the particles may bond by solid-state bonding but not melt. However, this approach is undesirable for the production of beta TCP ceramics, since at high temperatures beta TCP is converted to alpha TCP, which is not preferable for a bone replacement material.

Several patents describe the preparation of porous inorganic or ceramic structures using polymeric foams impregnated with a slurry of preformed ceramic particles. The prior art also describes the use of solution impregnated-polymeric foams to produce porous ceramic articles. The focus of this art is directed to the preparation of either metal or metal oxide foams and/or particles.

However, the above-described technologies are highly energy- and labor-intensive, involving several discrete time-consuming operations. Thus, while improvements have been made in ceramic processing technology leading to tricalcium phosphate biomaterials, improved preparative methods are still greatly desired.

SUMMARY OF THE INVENTION

Accordingly, the present invention provides improved methods of producing porous tricalcium phosphate (TCP) net-shaped materials or bodies. The present invention does not require the preparation of intermediate forms or the use of chemical steps to produce the final net-shaped material. Rather, the methods of this invention provide net-shaped compositions in essentially one step and in a significantly shortened time frame over methods known in the art. This invention is based on the novel use of combustion synthesis for producing TCP net shaped materials, and provides a means for forming such materials with better control of the porosity and the ratio of alpha and beta TCP in the final material.

More specifically, one aspect of this invention provides a method of producing a porous tricalcium phosphate net-shaped material having an intended final shape, said method comprising:

(a) preparing a reactant mixture comprising calcium oxide (CaO) and phosphorus pentoxide ($P_2O_5$), wherein the mole percent ratio of said calcium oxide and said phosphorus pentoxide allows the mixture to form tricalcium phosphate upon combustion;

(b) forming said reactant mixture into said intended final shape by placing said mixture into a combustible or noncombustible die having said intended shape and compressing said mixture;

(c) if said die is noncombustible, removing said formed reactant mixture from said die;

(d) igniting said formed reactant mixture to produce a net-shaped material having said desired shape by a combustion synthesis reaction, said material comprising alpha tricalcium phosphate or a mixture of alpha and beta tricalcium phosphate; and (e) optionally subjecting said net-shaped material to conditions sufficient to convert at least a portion of said alpha tricalcium phosphate to beta tricalcium phosphate.

In general; TCP formation occurs when the reactant mixture contains between about 60 and 90 mole percent CaO and between about 40 and 10 mole percent $P_2O_5$. In one embodiment the mole percent ratio of $CaO:P_2O_5$ in the reactant mixture is between about 66.7:33.3 and 88.9:11.1. The stoichiometry can be varied to adjust the amount of alpha and beta TCP in the combustion synthesis product. In one embodiment, the reactant mixture further comprises one or more dopants. The reactant mixture may further comprise a gasifying agent. The TCP combustion synthesis product may optionally be further treated in a controlled heating/cooling step to increase the amount of beta TCP relative to alpha TCP in the final net shaped TCP material.

Certain parameters may be also varied to control the porosity, the amount of interconnected pores, and pore shape of the final net-shaped material to facilitate the engineering of materials with desired porosities such as functionally graded porosities. Examples of such parameters include, but are not limited to, the amount of pressure used to compress the reactant mixture (i.e., the density of the compressed reactant mixture), the amount of gasifying agent, the stoichiometry of the reactant mixture, the particle size of the CaO and $P_2O_5$ powders, the pressure under which the reaction takes place (ranging from a total vacuum up to a high pressure such as 10 atm), and gravity (e.g., conducting the combustion synthesis in low gravity).

This invention further provides porous net-shaped TCP materials prepared by the methods of this invention. Pore size diameter can be in a range from less than 5 μm to greater than 1,000 μm. The materials can be uniformly or non-uniformly porous. In one embodiment, the non-uniform porosity is functionally graded.

The porous net-shaped TCP materials produced by the methods of this invention are useful in the repair and/or replacement of bone in orthopedic, craniofacial and dental procedures. Since the porous calcium phosphate scaffolding material of the present invention is biocompatible, osteogenesis can occur with the implanted TCP material. This leads to eventual bone infiltration and replacement of the calcium phosphate matrix with autologous bone tissue.

Additional advantages and features of this invention shall be set forth in part in the description that follows, and in part will become apparent to those skilled in the art upon examination of the following specification or may be learned by the practice of the invention. The features and advantages of the invention may be realized and attained by means of the instrumentalities, combinations, and methods particularly pointed out in the appended claims.

BRIEF DESCRIPTION OF THE FIGURES

The accompanying drawings, which are incorporated in and form a part of the specification, illustrate non-limiting embodiments of the present invention, and together with the description serve to explain the principles of the invention. In the Figures.

DETAILED DESCRIPTION OF THE INVENTION

Figure 1:
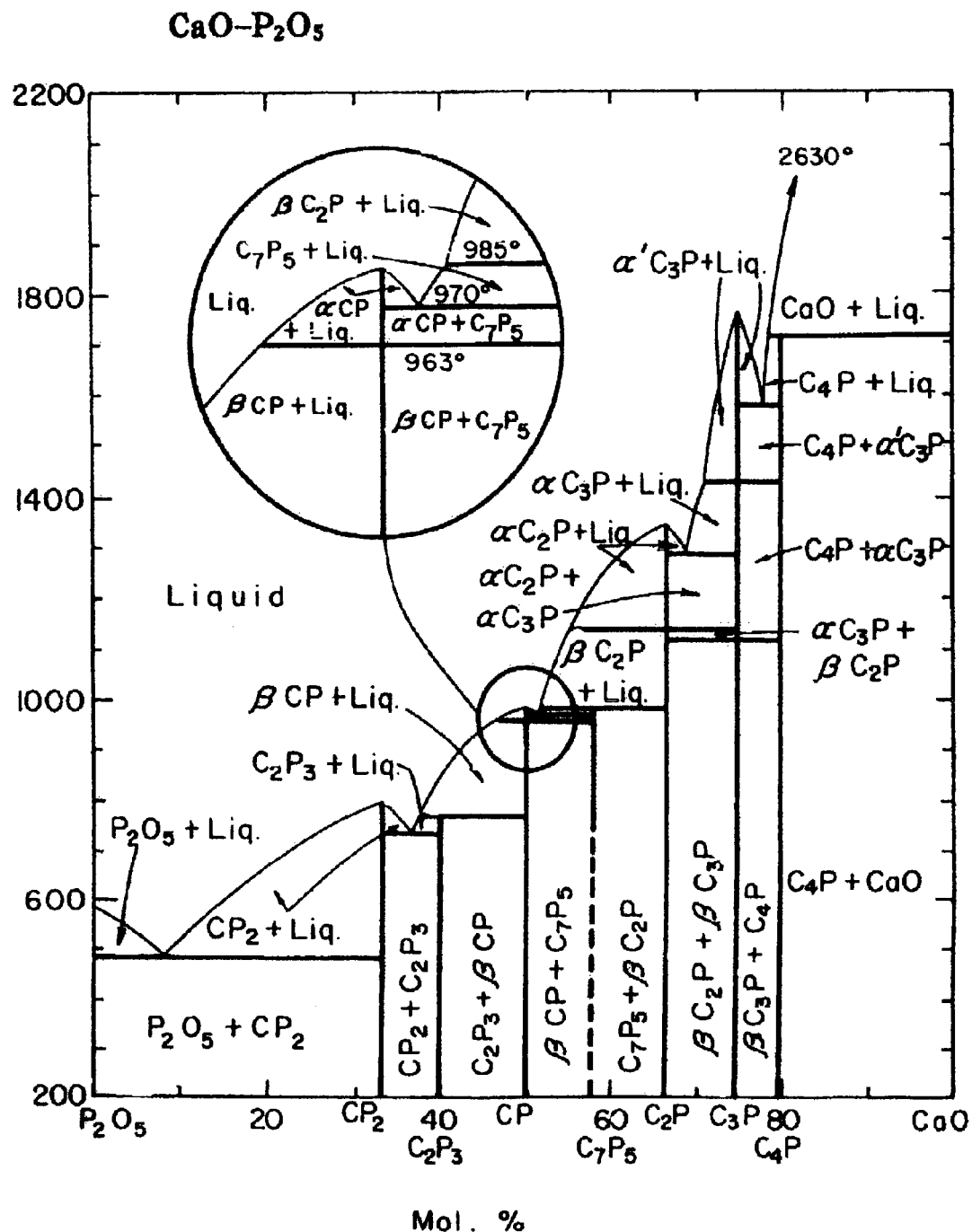
FIG. 1 is a $CaO$—$P_2O_5$ phase diagram provided as temperature versus mole percent CaO and $P_2O_5$.

In accordance with the present invention, methods of producing net-shaped or near net-shaped materials or bodies comprising tricalcium phosphate (TCP) are provided. In general, the method of the invention comprises preparing a mixture comprising calcium oxide and phosphorus pentoxide in a ratio that allows formation of tricalcium phosphate upon combustion thereof, forming this mixture into a green pellet having the desired final shape, and carrying out a combustion synthesis on the green pellet. The combusted pellet, comprising alpha TCP or mixtures of alpha and beta TCP, is optionally treated to effect transition of at least a portion of the TCP in the alpha form to the beta form. The stoichiometry as well as the reaction conditions can also be manipulated to control the ratio of alpha and beta forms of TCP in the final material appropriate for the intended use of the final material.

"Net-shaped" and "near-net-shaped" materials are those which require relatively little or no post-manufacturing processing (such as grinding, polishing, cuffing, deburring, etc.). That is, net-shaped or near-net-shaped materials are those whose final shape and dimensions may be largely or even completely achieved by the methods of this invention. For the purposes of this application, both "net-shaped" and "near-net-shaped" materials are referred to as net-shaped materials (the difference being largely one of degree). Some of the important advantages of net-shaped materials include, of course, minimizing or eliminating expensive post-manufacturing processing and machinery.

Overall, the present invention is advantageous in that shaped tricalcium phosphate (TCP) bodies may be formed easily, inexpensively, under carefully controllable conditions, and with enormous flexibility. Moreover, the microstructure of the inventive materials can be controlled as well, such that they emulate the morphological nature of natural bone.

The present invention also relates to net-shaped tricalcium phosphate materials comprising alpha TCP, beta TCP, or mixtures thereof made by the method of this invention. In another embodiment, the TCP materials of this invention further comprise one or more dopants.

It is preferred that the overall porosity of materials prepared in accordance with this invention be about 50-80%, although porosities less than 50% or greater than 80% are also within the scope of this invention. This characteristic is measured by pore volume, expressed as a percentage. Zero percent pore volume refers to a fully dense material having no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with W. D. Kingery, Introduction to Ceramics, p. 416 (Wiley, 1960), which provides a formula for determination of porosity. Expressing porosity as a percentage yields the pore volume. The formula is: Pore Volume=$(1-f_p)$ 100%, where $f_p$ is the fraction of theoretical density achieved.

Desired pore volumes are easily achieved in accordance with this invention. In one embodiment, the final product is a non-uniformly porous product. Preferably, the final product has a functionally graded, non-uniform porosity. A "functionally graded" non-uniform porosity refers to a controlled gradient without a specific interface from a given pore size and/or percent porosity to another pore size and/or percent porosity that has a specified alignment or direction within the net-shaped material.

Briefly, one embodiment of a method of this invention for preparing a porous tricalcium phosphate net-shaped material having an intended final shape comprises:

(a) preparing a reactant mixture comprising calcium oxide and phosphorus pentoxide in a mole percent ratio that allows the mixture to form tricalcium phosphate upon combustion;

(b) forming the reactant mixture into the intended final shape by placing the mixture into a combustible or noncombustible die having the intended shape and compressing the mixture;

(c) if the die is noncombustible, removing the reactant mixture from the die;

(d) heating the reactant mixture to at least the ignition temperature of said mixture to produce a net shaped material by a combustion synthesis reaction, wherein the material comprises alpha tricalcium phosphate or a mixture of alpha and beta tricalcium phosphate; and (e) optionally subjecting the net-shaped tricalcium phosphate material to conditions sufficient to convert at least a portion of the alpha tricalcium phosphate to beta tricalcium phosphate.

More specifically, the methods of this invention involve preparing a reactant mixture comprising calcium oxide and phosphorus pentoxide in a mole percent ratio such the mixture can form TCP upon combustion. In order to determine the proper mixtures of CaO and $P_2O_5$ required to form TCP, a CaO—$P_2O_5$ phase diagram was created as shown in FIG. 1. In FIG. 1, the alpha ($\alpha$) and beta ($\beta$) symbols are symbols commonly used in phase diagrams to denote fractional percentages of the constituents in a given region of the diagram, and therefore do not denote the actual presence of alpha and beta tricalcium phosphate. In general, TCP formation occurs when the reactant mixture contains between about 60 and 90 mole percent CaO and between about 40 and 10 mole percent $P_2O_5$. In one embodiment the mixture contains about 75 mole percent CaO and 25 mole percent $P_2O_5$.

The mole ratio of CaO and $P_2O_5$ can also be adjusted in order to obtain a net-shaped material having a ratio of the alpha and beta forms of TCP appropriate for the intended use (e.g., a craniofacial, dental, or orthopedic implant) of the TCP material. For example, when the TCP material is used as a bone implant, it is desirable to have a mixture of both the beta and alpha forms of TCP in the net shaped material. The alpha phase provides, strength to the TCP implant and allows for controlled absorption of the TCP material, while the beta phase allows for mineralization of the implant and release of specific ions such as calcium and phosphate as well as bioactive dopants such as silica. By adjusting the ratio of alpha and beta TCP, a more effective bone replacement scaffold can be prepared.

CaO and phosphorus pentoxide $P_2O_5$ are typically provided as reactant powders. The individual reactant powders are mixed together in the appropriate ratio to form the reactant mixture. Such mixing can be done by any method known in the art and the exact method of mixing is not critical to the invention, as long as an evenly distributed mixture is formed. One method includes placing the powders together in a ball mill and mixing under an argon atmosphere for approximately eight hours.

In one embodiment, dopants may added to the reactant mixture, provided that the dopant does not prevent formation of TCP. Suitable dopants for purposes of this invention include, but are not limited to, single element dopants such as zinc, and metal oxide dopants such as $Si_2$, $TiO_2$, $Al_2O_3$, MgO, $K_2O$, and NaO, or mixtures thereof. Dopants may be included as a means for increasing the bioactive nature of the TCP materials. For example, dopants can provide an appropriate localized microenvironment in a TCP implant that stimulates various bioactive processes in the body (e.g., thermodynamic/kinematic and biological mechanisms) such as biomineralization and cell signaling via membrane integrins. Further, dopants such as silica ($SiO_2$) may provide increased anabolic activity as a result of available orthosilicic acid to the fibroblast/osteoblasts cells (D. M. Reffitt, et al., *Bone* 32: 127-135 (2003)). Additionally, certain dopants provide increased structural integrity (e.g., reduced brittleness and increased ductility and strength) to the implant, and cause formation of hydroxyapatite on the surface of the TCP material. It has been hypothesized that the ability of TCP materials to bond to living bone may depend on the formation of a carbonate hydroxyapatite layer on the surface of the TCP material.

Dopants may also be added to the reactant mixture as yet another means to control the ratio of beta and alpha forms of TCP in the combusted material. For example, incorporation of a single element dopant such as Zn can change the amount of beta TCP in the combustion synthesis product through ion substitutions in the calcium phosphate crystal lattice. Metal oxide dopants such as titania, alumina, and silica can increase the amount of beta TCP in the combustion synthesis product by increasing the reaction temperature $T_c$, which in turn produces more beta TCP, as discussed below in detail.

After mixing the powders, the reactant mixture is formed into the desired net shape appropriate for the intended use, or into a shape sufficiently close to the desired final shape, such that relatively little post-manufacturing machining is required. For example, the net-shaped TCP materials may be used as orthopedic implants, e.g., in hip and knee replacements, as implants for craniomaximillofacial reconstruction, and as dental implants. Accordingly, examples of net shapes include, but are not limited to, joints, rods, pins, screws, plates, sheets, cones, pyramids, parallel piped blocks, disks, bowls, and a number of other shapes such as cylinders, platelets, long fibers, etc.

After placing the mixed reactant powder in the die, the powder is compacted or pressed to form a green pellet. The compaction pressure can be varied from less than one psi to greater than about 10,000 psi. The degree of compaction in part will determine the density and porosity of the final product. Therefore, the desired porosity of the final product can be achieved in part by varying the compaction pressure, and can be determined empirically with minimal experimentation.

The die can be either a combustible or noncombustible material, and the selection is not critical to the method of the invention. For example, it may be desirable to utilize a die made from a combustible material that will burn away during the combustion step. Examples of suitable combustible materials include, but are not limited to, biodegradable polymers, rice paper, and sucrose. Alternatively, a noncombustible die such as stainless steel may be used. In this embodiment, the TCP product is removed from the die before the combustion synthesis step.

The appropriate porosity for a particular application of the TCP net-shaped product can be determined by those skilled in the art. For example, natural bone has a porosity of approximately 30 to 500 μm. An appropriate porosity for a bone implant is that which allows for optimal tissue in-growth to provide for remodeling and bone growth, including mineralization, while allowing for other necessary qualities such as modulus matching between the TCP implant and extant bone. The appropriate porosity also provides means for delivering drugs such as cytokines, bone morphogenic proteins, and other bone affecting reagents.

Once the reactant mixture is formed and compressed into the net shape or near net shape, the formed mixture is ignited so as to initiate a combustion synthesis reaction, which leads to the production of tricalcium phosphate (TCP). A combustion synthesis reaction is an exothermic chemical reaction process that utilizes the excess heat/energy generated during a reaction (without additional energy input) to ignite unreacted portions of the mixture, thereby producing the desired final product. An advantage of using combustion synthesis to form the final product is that combustion synthesis is an efficient and economical process of producing materials.

Combustion synthesis can be performed using one of two modes. The first mode is a propagating mode, known in the art as "self-propagating high temperature synthesis," or "SHS." The main objective of SHS is to provide a steady state, propagating combustion wave in order to ensure complete conversion of the reactants into the desired product.

In a self-propagating combustion synthesis process (SHS), the combustion reaction is initiated by heating a small region of the compressed reactant mixture until this local region reaches the ignition temperature ($T_{ig}$), whereupon an exothermic reaction heats adjacent layers of material via a propagating combustion wave. The wave spontaneously propagates through the reactant mixture, converting reactants (CaO and $P_2O_5$) into product (TCP). In the self-propagating mode, the combustion wave can move through the compressed reactant mixture at a rate of 1 to 150 mm/s, depending on the reaction system. The maximum temperature reached is the combustion temperature $T_c$. Under adiabatic conditions, where no heat is lost to the surroundings, the maximum combustion temperature can be assumed to be the adiabatic temperature $T_{ad}$. The ignition temperature $T_{ig}$ for CaO—$P_2O_5$ reactant mixtures is typically about 1500° C. and combustion temperature $T_c$ is typically between about 1700 and 1800° C. These temperatures are in the range where TCP will form predominantly in the alpha form as a result of the rapid cooling rates.

SHS is thus initiated by introduction of a rapid heating flux (e.g., 500-3000 watts of power over 1-3 seconds) to the reactant mixture. This ignition step may be accomplished by means of an electric arc, electric spark, flame, welding electrode, microwaves, laser, or other means of initiating combustion synthesis. In one method, combustion synthesis is initiated by generating an energy flux induced via a tungsten coil. The current applied across the coil governs the energy flux. Power must be sufficient to ignite the reaction and can vary from 1-100 amps and 1-1000 volts depending on the specific geometry and reactant stoichiometry. The energy flux is applied for a time sufficient to ignite the reaction, preferably from about 1 to 10 seconds. The total time of the combustion synthesis reaction for most embodiments of the present invention will generally be on the order of 10-20 seconds.

The second method of initiating exothermic reactions for producing TCP materials is a simultaneous combustion mode. In this mode, the compressed reactant mixture is placed inside a furnace at a temperature above the ignition temperature $T_{ig}$. Accordingly, all parts of the compressed reactant mixture reach $T_{ig}$ at approximately the same time, at which point the exothermic reaction is initiated throughout the entire mixture. In other words, the combustion occurs simultaneously throughout the entire sample in a thermal explosion.

When the combustion synthesis step (either SHS or simultaneous combustion) is completed, a TCP material is obtained having the desired net shape or near net shape. As discussed above, the temperatures reached during the combustion synthesis typically produce a TCP material comprising a mixture of the alpha and beta phases, with the majority of the TCP being in the alpha form. Additionally, the combustion product may also contain hydroxyapatite and octacalcium phosphate. However, depending on the intended use of the TCP product, it may be desirable to have a greater portion (or all) of the TCP material in the beta phase. Accordingly, one embodiment of the method of this invention comprises optionally subjecting the TCP combustion synthesis product to conditions sufficient to convert at least a portion (e.g., at least 1%) of the TCP from the alpha phase to the beta phase. As shown in the phase diagram in FIG. 1, the higher temperature phase is the alpha (monoclinic) phase, the lower temperature phase is the beta (orthorhombic) phase, and the conversion temperature between alpha and beta phases of TOP (i.e., the alpha/beta transition temperature) is approximately 1260° C. at 75 mol % calcium. At this temperature it is predicted that the TCP material will comprise approximately equal amounts of alpha TCP and beta TCP. Therefore, if the TCP product is heated to a high temperature and then cooled quickly, the fast cooling rate will preferentially yield the alpha phase. Alternatively, if the TCP product is heated to a high temperature and then cooled slowly, the slower cooling rate will preferentially yield the beta phase. Thus, it was discovered that the composition of the TCP final net shaped product (i.e., the relative amounts of alpha and beta TCP in the final product) can in part be manipulated by controlling the cooling rate of a heated TCP combustion synthesis material.

Accordingly, one method for increasing the amount of beta TCP relative to alpha TCP in a material obtained after combustion synthesis comprises placing the TCP combustion synthesis product in a furnace which is then heated to (or is already at) a temperature between about 1100 and 1600° C., followed by cooling the material under controlled conditions. For example, in one embodiment, the combustion product is heated in a furnace at 1260° C. or greater for a sufficient period of time, e.g., between about 5 and 120 minutes. In another embodiment, the combustion product is heated in a furnace that is just below 1100° C. for one or more hours. In any of the methods of this invention, the furnace may be heated up to the desired temperature at a rate of 40° C. per minute, although other heating rates may be used as well. The furnace is then cooled with the material inside the furnace at a controlled rate such that a desired amount of alpha TCP is converted to beta TCP. Alternatively, the TCP combustion synthesis product can be heated in a furnace as described, and then removed from the furnace and cooled to room temperature in ambient air to convert at least a portion of the alpha TCP to beta TCP. As stated, the cooling rate in part determines the relative amounts of alpha and beta TCP in the final net-shaped material. In addition, the amount of time the combustion synthesis TCP product is maintained in the heated furnace can also be adjusted to vary the amount of TCP in the beta phase relative to the alpha phase.

In another embodiment, the TCP material obtained after combustion synthesis can be treated to produce a TCP net shaped final product comprising a gradient of the beta form of TCP. According to this method, specific regions of the TCP combustion synthesis material can be treated, for example, via laser or microwave to produce greater amounts of beta TCP in the treated regions. In this manner, the composition of the final net-shaped product can be specifically designed, for example, to mimic the tissue (e.g., bone) into which the product will be implanted.

In yet another embodiment, the combustion synthesis step as well as the subsequent heating and controlled cooling steps can be performed in the same furnace as a means for producing a TCP net shaped product having the desired ratio of beta/alpha TCP. More specifically, another method of this invention for preparing a TCP net-shaped material comprises (a) preparing a reactant mixture comprising calcium oxide and phosphorus pentoxide, wherein the mole percent ratio of said calcium oxide and said phosphorus pentoxide allows the reactant mixture to form tricalcium phosphate upon combustion;

(b) forming said reactant mixture into said intended final shape by placing said mixture into a combustible or noncombustible die having said intended shape and compressing said mixture;

(c) if the die is noncombustible, removing said formed reactant mixture from said die;

(d) rapidly heating said compressed reactant mixture in a furnace at a temperature sufficient to produce a net-shaped material by a simultaneous combustion synthesis reaction, said material comprising alpha tricalcium phosphate or a mixture of alpha and beta tricalcium phosphate; and (e) either reducing the temperature of the furnace at a controlled rate or removing the combustion synthesis product from the furnace and cooling at room temperature to convert at least a portion of the alpha TCP to beta TCP.

As used herein, "rapid heating" refers to a heating rate of at least 10 degrees Celsius per minute. An extreme example is "instantaneous" heating using a high-powered laser tightly focused on a small region.

Another variable that can be manipulated as a means of increasing the amount of beta TCP relative to alpha TCP in the final TCP net shaped material is the addition of a dopant to the reactant mixture prior to the combustion synthesis step. For example, incorporation of single element dopant such as Zn can change the amount of beta TCP through ion substitutions in the calcium phosphate crystal lattice. Metal oxide dopants such as titania, alumina, and silica can be added increase the amount of beta TCP in the product obtained upon combustion by lowering the reaction temperature $T_c$, which in turn produces more beta TCP in the combustion synthesis product. If the combustion synthesis product obtained has the desired amount of beta TCP, the heating/cooling treatment of the synthesis product to convert alpha TCP to beta TCP is not necessary.

Figure 2:
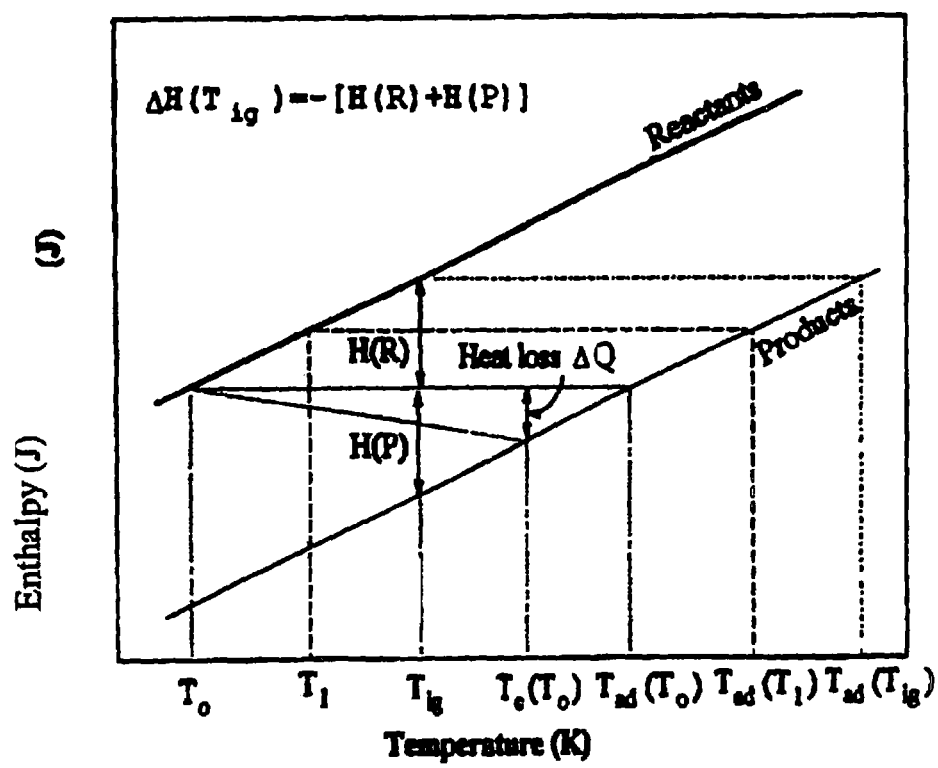
FIG. 2 shows X-ray diffraction patterns of net-shaped TCP materials after subjecting the materials to different conditions for converting alpha TCP to beta TCP.

FIG. 2 shows three X-ray diffraction patterns of TCP materials prepared using the SHS combustion mode and subsequently subjected to various conversion conditions. The X-ray diffraction patterns show the relative amounts of alpha TCP and, beta TCP in the net-shaped product after the conversion step. Spectrum A was obtained from a TCP sample that was produced via SHS and then cooled in the SHS reaction chamber. Under these conversion conditions, the final material produces a spectrum that is representative of the powder diffraction file 70-0364 for alpha TCP (monoclinic), indicating that virtually all the TCP is in the alpha form. Spectrum B was obtained from a TCP sample that was produced via SHS, then heated to 1100° C. at rate of about 40° C./minute in ambient air and subsequently removed from the furnace and cooled in ambient air. Spectrum B shows that the major peak representing alpha TCP and the major peak representing beta TCP are present in almost equal proportions. Spectrum C was obtained from a TCP sample that was produced via SHS, then heated to 1100° C. at rate of about 40° C./minute in ambient air and subsequently cooled in the furnace in ambient air at a rate of 3° C. per minute. Spectrum C shows that almost all of the alpha phase was eliminated and the majority of the TCP net-shaped material, i.e., approximately 95%, is in the beta phase.

Figure 3:
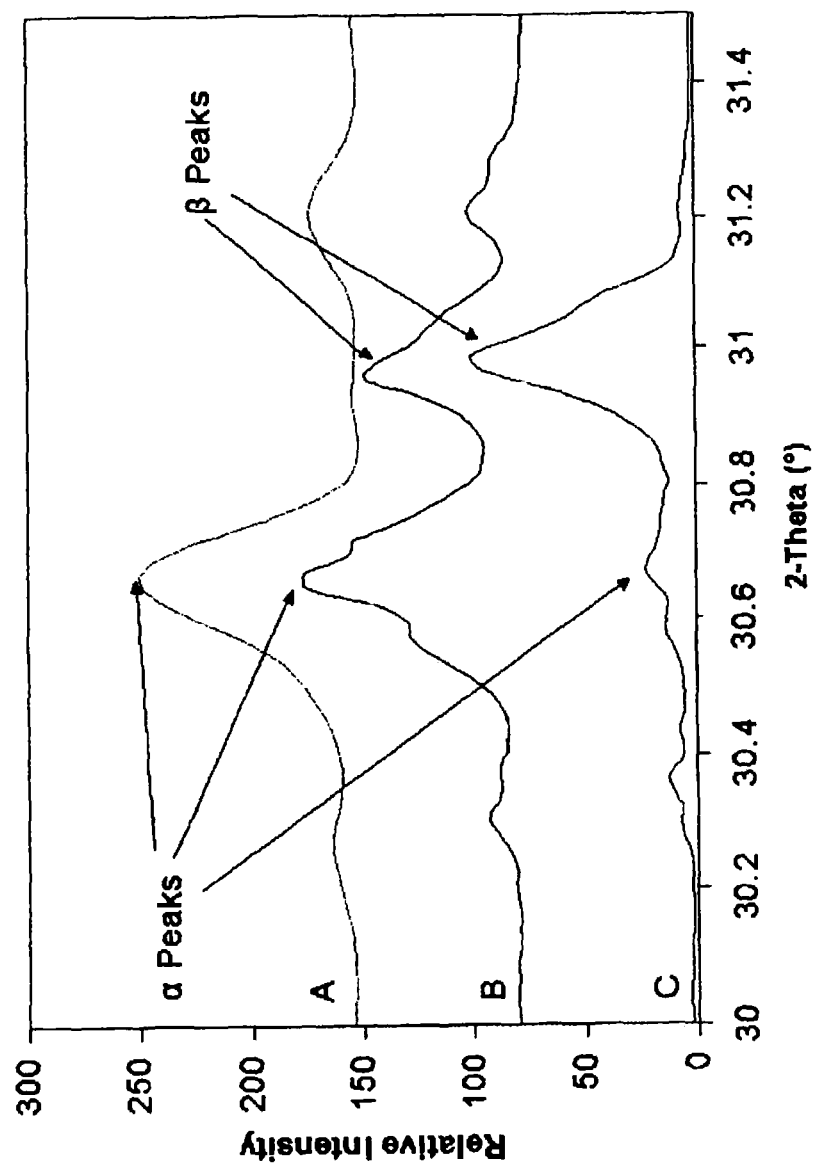
FIG. 3 is a theoretical temperature-enthalpy diagram used to determine appropriate conditions for SHS reaction systems.

FIG. 3 shows a temperature-enthalpy diagram that can be used to determine the adiabatic temperature for combustion synthesis reactions. In the self-propagating combustion synthesis mode, the reactant mixture has to be heated from the initial temperature $T_o$, (e.g., 298K) to the ignition temperature $T_{ig}$, in order to initiate the combustion synthesis reaction. The resulting exothermic reaction initiated at $T_{ig}$ generates heat which results in a maximum theoretical adiabatic temperature, $T_{ad}(T_o)$. However, some of the heat generated at the reaction front is needed to raise the temperature of the next adjacent reactant layer from $T_o$ to $T_{ig}$. This amount of heat, H(R), is also indicated in FIG. 3. Since the reaction is initiated at $T_{ig}$, the heat of reaction is $\Delta H(T_{ig})$, i.e., the difference between the enthalpy of the products at $T_{ig}$ and that of the reactants at $T_{ig}$. Therefore the balance of $\Delta H(T_{ig})$, i.e. $\Delta H(T_{ig})$–H(R), is the amount of heat available to heat the products from $T_{ig}$ to $T_{ad}$ ($T_o$) and can be designated as H(P), such that, using the normal sign convention for enthalpy:

$$\Delta H(T_{ig}) = -[H(R)+H(P)]$$

Pre-heating the reactants above $T_o$, e.g. to $T_1$, will decrease H(R) and increase H(P), thus increasing the adiabatic temperature to $T_{ad}(T_1)$. Increasing the pre-heat to $T_{ig}$ (i.e. the simultaneous combustion mode), will decrease H(R) to zero and increase the adiabatic temperature to $T_{ad}(T_{ig})$, the maximum adiabatic temperature achievable with this reaction system. The alternative thermochemical calculation of $T_{ad}$ uses the relationship:

$$\Delta H(298) + \int_{298}^{T_{ad}(298)} \sum n_j C_p(P_j) \, dT + \sum_{298-T_{ad}(298)} n_j L(P_j) = 0,$$

where the only unknown is $T_{ad}(298)$.

Typical recorded combustion temperatures $T_c$ will vary from the theoretical adiabatic temperature as the difference between $T_o$ and $T_{ig}$ increases, since under this conditions there is more opportunity for heat loss, i.e., $\Delta Q$ (see FIG. 3) from the reaction front. In the simultaneous combustion mode, $T_c$ should approximate to $T_{ad}(T_{ig})$. It has been empirically determined that a reaction will be self-sustaining if $T_{ad}$>1800K and $$\Delta H(298K)/C_p(298K) \geq 2000.$$

Figure 4:
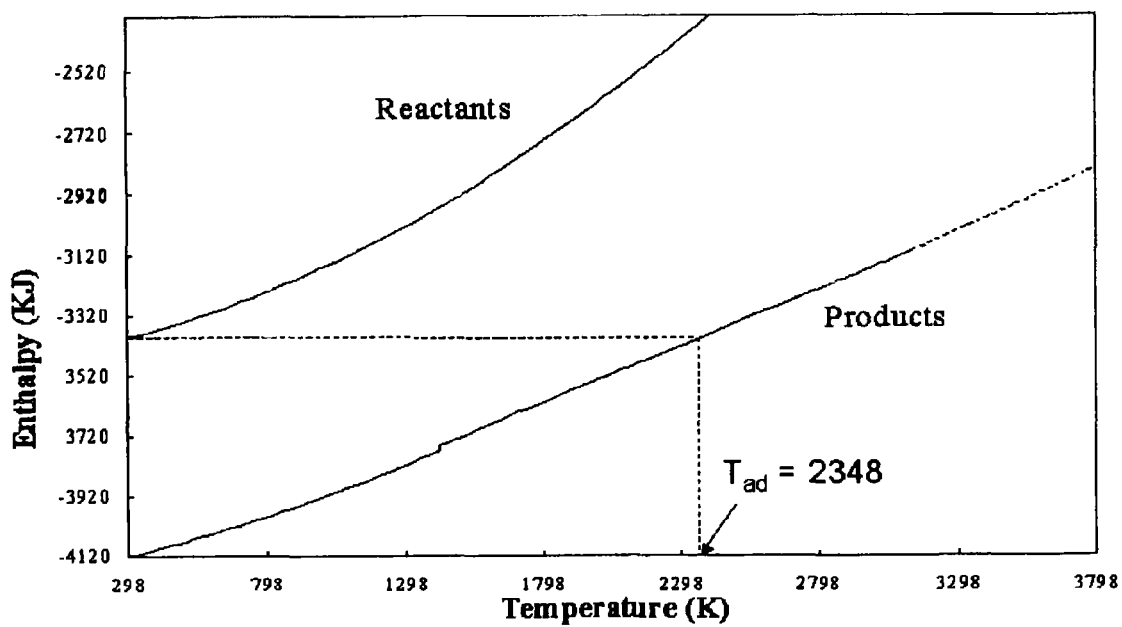
FIG. 4 is a temperature-enthalpy plot for the combustion synthesis of TCP from CaO and $P_2O_5$.

FIG. 4 shows the graphical determination of the thermochemistry for tricalcium phosphate as measured from experimental data generated by the inventors, which allows for determination of the maximum theoretical adiabatic temperature $T_{ad}$.

Another aspect of the present invention provides net-shaped tricalcium phosphate materials made by the processes of this invention comprising alpha TCP, beta TCP, or mixtures thereof. In one embodiment, the TCP materials of this invention further comprise one or more dopants including, but not limited to, single element dopants such as zinc and metal oxide dopants such as $SiO_2$, $TiO_2$, $Al_2O_3$, MgO, $K_2O$, and NaO, or mixtures thereof. TCP net-shaped bodies of this invention can exhibit considerable pore volume (e.g. 40-60%) when the reactants and products remain in the solid state. This porosity results largely from the initial porosity in the compressed reactant mixture and the change in volume that takes place between the products and reactant species during the combustion synthesis reaction. If the combustion temperature exceeds the melting point of the product(s) phase(s), densification of the product material can take place due to solidification. It is preferred that the overall porosity of materials prepared in accordance with this invention be at least about 50-80%. Such pore volumes are easily achieved in accordance with this invention. Pore size diameter can be in a range from less than 5 µM to greater than 1,000 µm. The net-shaped materials may have interconnecting (open) pores or closed pores, or may contain a combination of open and closed pores.

The porosity of the TCP net-shaped materials can also be adjusted by adding a gasifying agent or volatizing medium to the reactant mixture. $P_2O_5$ and $B_2O_3$ are examples of in-situ gasifying agents suitable for use in the methods of this invention. When the gasifying agent is released at the combustion front at approximately the same time that the liquid phase is formed, there is a potential produce a final product having increased porosity. As used herein, "increased porosity" refers to the increase in the percentage of pores in the final product.

However, there must be a balance between the timing of the release of the gasifying agent and the generation and physiochemical properties (e.g. the viscosity and/or plasticity) of the liquid phase. For example, there needs to be an optimum level of resistance to the transport of the gas produced by the gasifying agent through the liquid phase. If this resistance is too high (i.e., is the liquid has a high viscosity) the gas becomes entrapped in the liquid and remains there during subsequent solidification, typically resulting in large "blow holes" in the product. If the resistance is too low (i.e., is the liquid has a low viscosity) the gas will easily pass through the liquid without causing an increase in porosity upon subsequent solidification of the liquid phase. This latter condition can also arise if the gas is generated well before or well after the generation of the liquid phase. In addition, there is an optimum volume fraction of the liquid phase that must be generated in order for the gas to be effective in increasing the extent of the porosity in the product. Therefore, this balancing of gas generation with a maximum liquid generation of sufficiently high plasticity at the propagating combustion front must be designed into the combustion synthesis reaction system in order to engineer appropriate the porosity as well as the mechanical and material properties for the intended use of the TCP net-shaped material.

Other factors that may be employed in the methods of this invention to engineer the required microstructure and porosity in the TCP materials include, but are not limited to, (1) controlling the adiabatic temperature and, hence the combustion temperature of the combustion synthesis reaction, (2) preheating the reactant mixture, which increases $T_{ad}$ and $T_c$, and/or (3) adding a diluent such as previously reacted $Ca_3(PO_4)_2$ to the reactant mixture, which decreases $T_{ad}$ and $T_c$.

The TCP materials produced by the methods of this invention are either uniformly or nonuniformly porous. For example, the net shaped TCP material may have a uniform porosity throughout its entire structure. Alternatively, the TCP material may have a finite number of concentric or stacking layers having varying porosities with respect to each other (i.e., a gradient porosity), with transitions from one pore size to another occurring across the entire implant or within specific sections. A number of factors can be varied to alter the pore size of the final product, including varying the reactant particle size (typically from about 10 microns up to 100 microns) and the amount of gasifying agent (e.g., $P_2O_5$), as well as adding one or more diluents such as a dopant.

A TCP net-shaped of this invention may also have a functionally graded non-uniform porosity, wherein "functionally graded" means that the transition from one porosity to another is smooth with no abrupt transitions. A functionally graded porosity may follow a linear transition between porosities. Alternatively, more complex net-shaped materials are provided having functional gradients that may be described logarithmically or exponentially.

On method for producing a TCP net-shaped body having non-uniform porosity comprises "stacking" layers of TCP material, each having different porosities. For example, to create a gradient of finite layers, a first layer is prepared according to this invention by preparing a first reactant mixture with the appropriate stoichiometry, powder size, dopants, etc., to produce a combustion synthesis product having a first pore size. The first reactant mixture is pressed into a net shape with the appropriate pressure for the desired pore size, then combusted and cooled to yield a first combustion synthesis layer having a first pore size. A second reactant mixture with the appropriate stoichiometry, powder size, dopants, etc., to produce a combustion synthesis product having a second pore size is prepared and placed on top of the first combustion reaction product. The second reactant mixture is pressed into a net shape with the appropriate pressure for the desired pore size and then combusted to produce a second layer adjacent the first layer and having a second pore size that is different than the first pore size. Additional layers can be added in the same manner as desired to create the final article having non-uniform porosity. In an alternative method, the first reactant mixture, second reactant mixture, etc. can be layered first and then pressed simultaneously.

In another embodiment, the above-described method for preparing a TCP material having non-uniform porosity can be modified to product a TCP material having a functionally graded non-uniform porosity. For example, in one embodiment a functionally graded porosity is achieved by forming two or more layers of uncombusted (green) reaction powders, placing one powder on top of the other in a die, and compressing the layers. Each layer will have an appropriate stoichiometry, powder size, dopants, etc., to produce the desired porosity. The layered material is then combusted as described herein to produce the TCP net-shaped material by combustion synthesis having a functionally graded non-uniform porosity.

Figure 5:
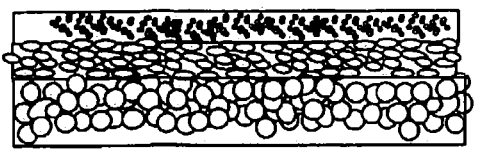
FIG. 5 is an illustration of a TCP net-shaped material having a one-dimensional non-uniform porosity.
Figure 6:
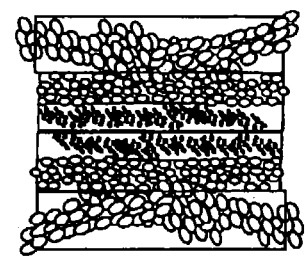
FIG. 6 is an illustration of a TCP net-shaped material having a two-dimensional non-uniform porosity.

In one embodiment the TCP net-shaped material has a one-dimensional non-uniform porosity such as that shown in FIG. 5. FIG. 5 illustrates a non-limiting example of a three layered TCP net-shaped final product wherein the pore size increases from top to bottom. However, it will be understood that a TCP net-shaped final product such as that shown in FIG. 5 can have fewer or greater than three layers, and further the pore size of each layer can be larger or smaller than that of the adjacent layer. Alternatively, the TCP net-shaped final product can have a two-dimensional non-uniform porosity such as that shown in FIG. 6. FIG. 6 illustrates a non-limiting example of a TCP net-shaped product having six layers, wherein the two internal layers have the smallest pore sizes, and each adjacent layer extending from the internal layer has an increasingly larger pore size. However, it will be understood that a TCP net-shaped final product such as that shown in FIG. 6 can have fewer or greater than six layers, and further the pore size of each layer can be larger or smaller than that of the adjacent layer.

Figure 7:
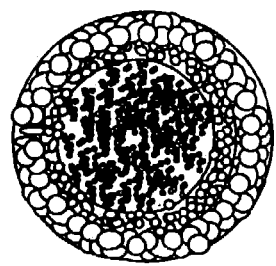
FIG. 7 is an illustration of a TCP net-shaped material having a radial non-uniform porosity.

Another method of this invention produces a TCP net-shaped product having a 2 dimensional radial porosity gradient, such as that shown in FIG. 7. In one embodiment, a radial porosity gradient is achieved by preparing a first layer of a first reactant mixture with the appropriate stoichiometry, powder size, dopants, etc. to produce a layer having first pore size upon combustion. The first reactant mixture is pressed into a net shape with the appropriate pressure for the desired pore size, then combusted and cooled to yield a first combustion synthesis layer having a first pore size. This first combustion synthesis layer can then be placed into another die and a second reactant mixture with the appropriate stoichiometry, powder size, dopants, etc. to produce a second pore size can be placed around the first compressed reactant mixture, followed by a second pressing at a second pressure to form a second (outer) compressed reactant mixture layer. Upon combustion synthesis of this second compressed reactant mixture, a net-shaped material having a radial gradient porosity is obtained. Additional radial layers can be added as needed to prepare the desired final product. In another embodiment, radial layers of green reactant mixtures are formed within the die and then combusted at the same time to provide a TCP net-shaped material having a radial, functionally graded non-uniform porosity. In this embodiment, the layers can be compressed individually after adding each layer to the die or at once after all of the layers have been added to the die.

It is to be understood that the above-described methods are used for illustrative purposes only and are not meant to be limiting to the methods and materials of this invention. Thus, many other methods may be used for forming non-uniformly porous TCP net-shaped materials, and such methods are included in the present invention.

The net-shaped TCP materials of this invention may be used in a wide variety of applications, especially in surgery (e.g., craniofacial implants) dentistry, and orthopedics, where their properties of biocompatibility, osteogenic stimulation, and inherent strength will be found to be beneficial. Examples of net shapes suitable for such purposes include, but are not limited to, joints, rods, pins, or screws, plates, sheets, cones, pyramids, parallel piped blocks, disks, bowls, and a number of other shapes such as cylinders, platelets, long fibers, etc.

For example, the TCP net-shaped materials of this invention may be employed to provide strength and stability to injured joints, fractured bone, etc. When the materials of this invention are used in bone replacement applications, there needs to be a maximum amount of open pores in a bone replacement material to facilitate bone in-growth, transportation of nutrients, and subsequent maturation of bone in the pore spaces. In use, such pins, screws, rod, etc., are inserted into a prepared location and cemented into place. Unlike prior, generally metallic, pins or rods, however, the TCP net-shaped materials of the present invention are inherently biocompatible and, indeed, osteostimulatory. A particular advantage of the present methodology is that after healing of the situs of the restoration or implant, the implanted TCP material will begin to adhere chemically to bone tissue interface, increasing the strength and toughness of the implant system.

TCP net-shaped materials of the present invention may also be used in a wide variety of restorative and surgical procedures including those involving bone tissue subject to large forces. One example is the repair or fusion of vertebrae of the spine. A net-shaped material produced according to this invention can be placed in or near the spine to provide load-bearing stability and micromechanical bonding to vertebrae or other bony material. After some time in the body, tissue and bone attachment become augmented through the biological interfacial chemical bond that eventually forms a hydroxyapatite biologic interfacial bond between tissue, bone, and the composite.

A further use of the TCP net shaped materials of the present invention can be found in endodontics. It is conventional to employ "points" for the restoration of root canals and the like. Such points are conventionally silver, gutta percha, or certain other materials. To restore a root canal, access to the root canal of a diseased tooth is obtained through the enamel and dentin of the tooth and a portion of the nervous, bony, and other tissue of the root canal is removed through the use of a number of conventional instruments. The actual preparation of root canals for restoration forms no part of the present invention and all such aspects of the procedure are well understood by persons skilled in the art. In accordance with the present invention, endodontic "points" can be prepared using the methods of this invention. These can then be inserted into the excavated space of a root canal. Substantially complete filling of the prepared root canal space can be attained and the osteostimulatory characteristic of the present materials can give rise to improved biocompatibility, and integration of the restoration into the patients bony structure, ensuing good results.

The methods of this invention provide several advantages over methods known in the art for preparing TCP net-shaped materials. For example, the methods of this invention can more accurately control material parameters of the net-shaped materials including porosity, surface chemistry, and structural material modulus. One benefit of controlling these parameters includes the production of materials that more effectively integrate with the physiological process of mineralization in vivo. For example, the TCP net-shaped materials made by the process of this invention are readily converted to appropriate forms of calcium phosphate such as hydroxycarbonate apatite, hydroxyapatite, and octacalcium phosphate (see Example 1). Yet another benefit of the method of this invention is that the materials so produced more effectively mimic the morphological natures of bone through appropriate pore sizes, porosity gradients, and pores shapes. Further, by utilizing the rule of mixtures, the process of this invention produces material bone implants that mimic the structural mechanical nature of bone and have elastic module conducive to the physiological function of bone. This has the advantage of increasing implant mechanical stability and reducing stress-shielding (bone resorption as a result of the modified load environments where bone that has little or no strain is resorbed). The rule of mixtures is a standard materials equation that relates the apparent Elastic Modulus ($E_{app}$) of a composite with that of its constituents based upon their relative volume occupied. Thus, $E_{app}=E_{s1}(V_{s1})+E_{s2}(V_{s2})+\ldots$. In the case of a porous material, this equation reduces to $E_{app}=E_{solid}(1-\text{porosity})^n$, where n=1 or 2 depending upon the porosity. For example, for a highly porous material (e.g., 80% or greater porosity), n=2. A TCP net-shaped final product of this invention will have a modulus of elasticity ranging from about 4-20 GPa, as determined by the rule of mixtures and depending on the porosity.

The TCP net-shaped materials made by the process of this invention are more advantageous over other bone replacement materials in the art in that they are more effectively resorbed by the body as they replaced with bone tissue through dissolution of the material, phagocytosis, and or other mechanisms.

The invention may be better understood with reference to the accompanying examples that are intended for purposes of illustration only and should not be construed as, in any sense, limiting the scope of the present invention, as defined in the claims appended hereto. While the described procedures in the following examples are typical of those that might be used, other procedures known to those skilled in the art may alternatively be utilized. Indeed, those of ordinary skill in the art can readily envision and produce further embodiments, based on the teachings herein, without undue experimentation.

Example 1

Interaction of TCP Materials with Simulated Body Fluids

This experiment characterized calcium phosphate based ceramics produced via the Self-Propagating High Temperature Combustion Synthesis (SHS) method and elucidated the activity of the products after soaking in a simulated body fluid.

Five reactant mixtures (S1-S5) were prepared with compositions shown in Table 1. The reactant powders had the following characteristics: CaO (325 mesh, 99.99% pure), $P_2O_5$ (100 mesh, 99.99% pure), $SiO_2$ (325 mesh, 99.6% pure), $TiO_2$ (325 mesh, 99.99% pure), $Al_2O_3$ (325 mesh, 99.99% pure), and MgO (325 mesh, 99.99% pure).

TABLE 1

| System | S1 | | | S2 | | |
|---|---|---|---|---|---|---|
| Chemical | CaO | $P_2O_5$ | | CaO | $P_2O_5$ | $SiO_2$ |
| Wt % | 54.24 | 45.76 | | 45.45 | 38.35 | 16.25 |
| System | S3 | | | S4 | | |
| Chemical | CaO | $P_2O_5$ | $TiO_2$ | CaO | $P_2O_5$ | $Al_2O_3$ |
| Wt % | 43.15 | 36.4 | 20.45 | 40.82 | 34.44 | 24.74 |
| System | S5 | | | | | |
| Chemical | CaO | $P_2O_5$ | MgO | | | |
| Wt % | 48 | 40.49 | 11.5 | | | |

Each reactant mixture was mixed in an argon atmosphere due to the strong hygroscopic nature of the $P_2O_5$ and pressed into a cylinder of ($\Phi$=12 mm and h=18 mm. Each cylinder was reacted via the SHS method in argon gas and allowed to cool in air. The resultant products were sectioned into four equal parts and the second part from the top of the sample was ground into powder form using a pestle and mortar and sieved manually to a particle size of <53 μm.

The product powders were studied by the following techniques: XRID, FTIR, and SEM. The XRD patterns were obtained by a Siemnes Kristalloflex-810 using Cu Kα in θ-2θ scans. FTIR spectra were obtained in a Nicolet IR spectrometer after mixing 1 mg of powder with 200 mg of KBr and compacting at 800 MPa for 1 minute. The SEM study was conducted on a Personal SEM 2000 RJ Instrument. The powders were carbon coated to avoid peak overlap of one gold peak with the K line of phosphorus.

In order to evaluate the effect of a physiological environment on each product powder, 5 mg of each of the 5 powders was individually soaked in 10 mL of synthetic body fluid (SBF) at 37° C. for 10 days under static conditions. The SBF solution, which simulates the inorganic part of human blood plasma, was made by dissolving reagent-grade NaCl, $K_2HPO_4$, $MgCl_2$, $CaCl_2$, and $Na_2SO_4$ in deionized water and buffering to a pH of 7.25 with tris-(hydroxymethyl)aminomethane (THAM). After the ten-day soaking period, the powder surfaces were examined by XRD, FTIR, and SEM techniques.

XRD analysis indicated that the powders possess a low degree of crystallinity due to the presence of slightly broadened peaks. This is valid for both the as-synthesized product powders and those treated in SBF for ten days. The SEM analyses confirmed this conclusion. XRD of the as-synthesized product powders showed that system S1 primarily comprised alpha-TCP, while systems S2-S5, doped respectively with $SiO_2$, $TiO_2$, $Al_2O_3$, and MgO, presented peak matches for both the alpha and beta phases of TCP. For the S1 product powder that was soaked in SBF, the XRD pattern indicated that no hydroxyapatite (HA) structure was present on the surface of the powder. In contrast, the spectra for systems S2-S5 after soaking in SBF showed the presence of peaks pertaining to both hydroxyapatite (HA) and carboxyapatite (HCA) indicating a change in the material due to the SBF treatment.

FTIR analyses of both the untreated and treated sample showed similar trends to the above XRD results. The spectra of the untreated samples from systems S2-S5 showed characteristic wave numbers of both the alpha TCP phase (1186.0 $cm^{-1}$ and 582.6 $cm^{-1}$) and beta TCP phase (970.4 $cm^{-1}$ and 1119.2 $cm^{-1}$). FTIR analysis of all treated powders showed wave numbers from both the alpha and beta TCP phases in addition to wave numbers indicative of the presence of hydroxyapatite (HA) (1043.80 $cm^{-1}$ and 602.90 $cm^{-1}$).

All systems showed the presence of hydroxyapatite when places in a simulated body ionic solution, indicating a potential bioactive nature. However, the systems doped with $TiO_2$, $SiO_2$ and $Al_2O_3$ showed a greater amount of hydroxyapatite (mineral phase of bone). Hydroxyapatite in solution is formed via a solution reaction comprising the intermediate phases of amorphous calcium phosphate, tricalcium phosphate, and octacalcium phosphate. The hydroxyapatite measured for systems S1 and S2 (undoped and doped with MgO, respectively) is the hydroxyapatite of the substrate powder formed in the initial combustion synthesis reaction.

The SEM photographs indicated strong morphological changes on the surfaces of the powders after SBF treatment, in particular with respect to systems S2-S4. This was not the case for system S1. However, salt crystals were observed on the surface of the S1 powders, suggesting that an ionic exchange occurred between the powder and the SBF. Fewer globular structures were observed on the surface system of S5.

In conclusion, XRD, FTIR, and SEM analytical techniques show that after the ten-day SBF treatment substantial changes occur to the surface of the powders as evidence by the formation of HA/HCA globular structures. The presence of $SiO_2$, $TiO_2$, and $Al_2O_3$ appear to enhance the formation of an HA/HCA film on a TCP substrate placed in SBF, while the lack of such constituents or the presence of a more reactive component (MgO) appears to inhibit the formation of such a layer.

The formation of an HA/HCA film may also be the result of the presence of beta TCP within the as-synthesized material. System S1 showed no presence of HA/HCA as evidence by XRD and SEM when treated. Previous studies suggest that this may be due to its predominant alpha TCP phase constitution. Thus, the calcium phosphate based materials manufactured via SHS are able to create HA/HCA films similar to those seen in earlier research. The ease With which dopants can be introduced into the SHS reaction systems suggests the capacity of this technique to produce both common and novel calcium phosphate based biomaterials.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of producing a porous tricalcium phosphate net-shaped material having an intended final shape, comprising:
   preparing a powder reactant mixture comprising calcium oxide powder and phosphorus pentoxide powder, wherein a mole percent ratio of said calcium oxide powder to said phosphorus pentoxide powder allows the powdered reactant mixture to form tricalcium phosphate upon subsequent combustion;
   forming said powder reactant mixture into said intended final shape by placing said powder reactant mixture into a combustible or noncombustible die having said intended final shape and compressing said powder reactant mixture to form a formed reactant mixture;
   if said die is noncombustible, removing said formed reactant mixture from said die; and
   heating said formed reactant mixture to at least an ignition temperature of said formed reactant mixture to produce said porous tricalcium phosphate net-shaped material by a combustion synthesis reaction, wherein said porous tricalcium phosphate net-shaped material is selected from the group consisting of an alpha tricalcium phosphate, a beta tricalcium phosphate and mixtures thereof.

2. The method of claim 1, wherein said powder reactant mixture comprises between about 60 and 90 mole percent calcium oxide and between about 40 and 10 mole percent phosphorus pentoxide.

3. The method of claim 1, wherein the mole percent ratio of the calcium oxide powder to the phosphorus pentoxide powder is from about 66.7:33.3 to about 88.9:11.1.

4. The method of claim 1, wherein the mole percent ratio of the calcium oxide powder to the phosphorus pentoxide powder is about 75:25.

5. The method of claim 1, wherein said powder reactant mixture further comprises at least one dopant.

6. The method of claim 5, wherein said dopant is selected from the group consisting of $SiO_2$, $TiO_2$, $Al_2O_3$, MgO, $K_2O$, NaO, Zn and mixtures thereof.

7. The method of claim 1, wherein said powder reactant mixture further comprises a gasifying agent.

8. The method of claim 7, wherein said gasifying agent is selected from the group consisting of phosphorus pentoxide and $B_2O_3$.

9. The method of claim 1, wherein said net-shaped material has a non-uniform porosity.

10. The method of claim 9, wherein said non-uniform porosity is functionally graded.

11. The method of claim 1, wherein the heating step is accomplished by applying a current from a tungsten filament to a specific site on said formed reactant mixture.

12. The method of claim 11, wherein said current is from about 1-1000 amps and is applied for about 1-10 seconds.

13. The method of claim 1, wherein the heating step is accomplished by placing said formed reactant mixture in a furnace and heating said furnace to a temperature above the ignition temperature of said formed reactant mixture.

14. The method of claim 1, wherein said porous tricalcium phosphate net-shaped material comprises said alpha tricalcium phosphate, and the method further comprising:
    subjecting said porous tricalcium phosphate net-shaped material to conditions sufficient to convert at least a portion of said alpha tricalcium phosphate to beta tricalcium phosphate.

15. The method of claim 14, wherein the step of subjecting said porous tricalcium phosphate net-shaped material to the conditions sufficient to convert the at least the portion of said alpha tricalcium phosphate to said beta tricalcium phosphate comprises:
    placing said porous tricalcium phosphate net-shaped material in a furnace;
    heating said furnace to a temperature between about 1100 and 1600° C.; and
    cooling said porous tricalcium phosphate net-shaped material at a rate that allows conversion of the at least a portion of said alpha tricalcium phosphate to said beta tricalcium phosphate.

16. The method of claim 15, wherein said furnace is heated at a rate of approximately 40° C. per minute.

17. The method of claim 15, wherein said cooling comprises reducing the temperature of said furnace at a cooling rate of 3° C. per minute.

18. The method of claim 17, wherein said temperature is reduced to approximately room temperature over a period of 2 to 3 hours.

19. The method of claim 15, wherein said cooling comprises removing said porous tricalcium phosphate net-shaped material from said furnace and allowing said porous tricalcium phosphate net-shaped material to cool in ambient air.

20. The method of claim 14, wherein the step of subjecting said porous tricalcium phosphate net-shaped material to the conditions sufficient to convert the at least a portion of said alpha tricalcium phosphate to said beta tricalcium phosphate comprises subjecting at least a portion of said porous tricalcium phosphate net-shaped material to microwave heating.

21. The method of claim 14, wherein the step of subjecting said net-shaped material to the conditions sufficient to convert the at least a portion of said alpha tricalcium phosphate to said beta tricalcium phosphate comprises applying a laser beam to at least a portion of said porous tricalcium phosphate net-shaped material.

22. A method of producing a porous tricalcium phosphate net-shaped material having at least two layers of different porosities, comprising:
    preparing a first powder reactant mixture comprising calcium oxide powder and phosphorus pentoxide powder, wherein a mole percent ratio of said calcium oxide powder to said phosphorus pentoxide powder allows the first powder reactant mixture to form tricalcium phosphate upon combustion;
    placing the first powder reactant mixture into a combustible or noncombustible die having an intended shape for the porous tricalcium phosphate net-shaped material and compressing the first powder reactant mixture to form a compressed first reactant mixture;
    if the die is noncombustible, removing the compressed first reactant mixture from the die;
    heating the compressed first reactant mixture to at least an ignition temperature of the compressed first reactant mixture to produce a first layer of material by a combustion synthesis reaction, the first layer of material having a first porosity, wherein the first layer of material is selected from the group consisting of an alpha tricalcium phosphate, a beta tricalcium phosphate and mixtures thereof, wherein the compressed first reactant mixture has a composition that results in the first layer of material having a first pore size;

preparing a second powder reactant mixture comprising calcium oxide powder and phosphorus pentoxide powder, wherein a mole percent ratio of the calcium oxide powder of the second powder reactant mixture to the phosphorus pentoxide powder of the second powder reactant mixture allows the second powder reactant mixture to form tricalcium phosphate upon combustion;

placing the second powder reactant mixture into a combustible or noncombustible die having the intended shape and compressing the second powder reactant mixture to form a compressed second reactant mixture;

if the die is noncombustible, removing the compressed second reactant mixture from the die;

placing the compressed second reactant mixture on the first layer of material to form a dual layer material; and heating the dual layer material to at least an ignition temperature of the second reactant mixture to produce the porous tricalcium phosphate net-shaped material, wherein the porous tricalcium phosphate net-shaped material comprises the first layer of material and a second layer of material, wherein the second layer of material is formed by a combustion synthesis reaction, wherein the second layer of material is fused to the first layer of material, wherein the second layer of material of said porous tricalcium phosphate net-shaped material has a second porosity, wherein the second layer of material is selected from the group consisting of an alpha tricalcium phosphate, a beta tricalcium phosphate and mixtures thereof, wherein a composition of the compressed second reactant mixture results in the second layer of material having a second pore size.

23. The method of claim 22, wherein said porous tricalcium phosphate net-shaped material comprises said alpha tricalcium phosphate, and the method further comprising:
subjecting the porous tricalcium phosphate net-shaped material to conditions sufficient to convert at least a portion of said alpha tricalcium phosphate in at least one of the first layer of material and the second layer of material to beta tricalcium phosphate.

24. A method of producing a porous tricalcium phosphate net-shaped material having at least two layers of different porosities, comprising:
preparing a first powder reactant mixture comprising calcium oxide powder and phosphorus pentoxide powder, wherein a mole percent ratio of the calcium oxide powder to the phosphorus pentoxide powder allows the first powder reactant mixture to form a tricalcium phosphate material having a first porosity when combusted;
placing the first powder reactant mixture into a combustible or noncombustible die having an intended shape for the porous tricalcium phosphate net-shaped material and compressing the first powder reactant mixture;
preparing a second powder reactant mixture comprising calcium oxide powder and phosphorus pentoxide powder, wherein the mole percent ratio of the calcium oxide powder of the second powder reactant mixture to the phosphorus pentoxide powder of the second powder reactant mixture allows the second powder reactant mixture to form a tricalcium phosphate material having a second porosity when combusted;
placing the second powder reactant mixture into the die on top of the first powder reactant mixture and compressing the second powder reactant mixture and the first powder reactant mixture to form a compressed mixture;
if the die is noncombustible, removing said compressed mixture from the die; and
rapidly heating said compressed mixture in a furnace at a temperature sufficient to produce the porous tricalcium phosphate net-shaped material by a combustion synthesis reaction, wherein the porous tricalcium phosphate net-shaped material is selected from the group consisting of an alpha tricalcium phosphate, a beta tricalcium phosphate and mixtures thereof.

25. The method of claim 24, wherein said porous tricalcium phosphate net-shaped material comprises said alpha tricalcium phosphate, and the method further comprising:
subjecting said porous tricalcium phosphate net-shaped material to conditions sufficient to convert at least a portion of the alpha tricalcium phosphate to beta tricalcium phosphate.

26. A method for preparing a tricalcium phosphate net-shaped material, comprising:
preparing a powder reactant mixture comprising calcium oxide powder and phosphorus pentoxide powder, wherein a mole percent ratio of said calcium oxide powder to said phosphorus pentoxide powder allows the powder reactant mixture to form tricalcium phosphate when combusted;
forming said powder reactant mixture into an intended final shape by placing said powder reactant mixture into a combustible die having said intended final shape and compressing said powder reactant mixture to form a compressed mixture; and
rapidly heating said compressed mixture in a furnace at a temperature sufficient to produce said tricalcium phosphate net-shaped material by a combustion synthesis reaction, wherein said tricalcium phosphate net-shaped material is selected from the group consisting of an alpha tricalcium phosphate, a beta tricalcium phosphate, and mixtures thereof.

27. The method of claim 26, wherein said tricalcium phosphate net-shaped material comprises said alpha tricalcium phosphate, and the method further comprising:
reducing the temperature of the furnace at a controlled rate to convert at least a portion of the alpha tricalcium phosphate to beta tricalcium phosphate.

* * * * *